(12) United States Patent
Kipshidze et al.

(10) Patent No.: US 11,771,437 B2
(45) Date of Patent: Oct. 3, 2023

(54) DUAL-PUMP SYSTEM FOR DELIVERING EMBOLIC BEADS OR OTHER THERAPEUTIC SUBSTANCES INTO AN ARTERY

(71) Applicant: Endobar Solutions LLC, Orangeburg, NY (US)

(72) Inventors: Nicholas Kipshidze, New York, NY (US); Jason Rahimzadeh, Dumont, NJ (US); Eran Levit, Amherst, NH (US)

(73) Assignee: Endobar Solutions LLC, Orangeburg, NY (US)

( * ) Notice: Subject to any disclaimer, the term of this patent is extended or adjusted under 35 U.S.C. 154(b) by 488 days.

(21) Appl. No.: 16/922,722

(22) Filed: Jul. 7, 2020

(65) Prior Publication Data

US 2022/0008083 A1 Jan. 13, 2022

(51) Int. Cl.
*A61B 17/12* (2006.01)
*A61M 5/142* (2006.01)
*A61M 5/168* (2006.01)
(Continued)

(52) U.S. Cl.
CPC ... *A61B 17/12186* (2013.01); *A61M 5/14232* (2013.01); *A61M 5/16813* (2013.01);
(Continued)

(58) Field of Classification Search
CPC .......... A61M 5/16854; A61M 5/16827; A61M 5/14232; A61M 5/16813; A61M 5/16881; A61M 39/22; A61M 39/28; A61M 39/283; A61M 39/284; A61M 39/285; A61M 39/286; A61M 2039/1083;
(Continued)

(56) References Cited

U.S. PATENT DOCUMENTS 4,802,650 A * 2/1989 Stricker .............. A61M 5/1408
251/117
9,572,700 B1 2/2017 Kipshidze et al.
(Continued)

FOREIGN PATENT DOCUMENTS

EP 3222305 B1 1/2019

OTHER PUBLICATIONS

International Search Report and Written Opinion issued in application No. PCT/US2021/040235 dated Oct. 18, 2021.

*Primary Examiner* — Nilay J Shah
(74) *Attorney, Agent, or Firm* — Potomac Law Group, PLLC

(57) ABSTRACT

A suspension of a therapeutic substance (e.g., embolic beads) dispersed within a liquid can be delivered via a catheter by using a bidirectional pump to rapidly draw the mixture of the therapeutic substance and liquid from an external syringe into an internal reservoir, then rapidly push the mixture back out into the external syringe. The rapid operation of the bidirectional pump mixes the two constituents so that the therapeutic substance is temporarily suspended within the liquid. Then, a low-speed pump is used to inject the mixture out via the catheter. In some embodiments, the parameters of the low-speed pump are controlled so that the fluid exiting the catheter will experience laminar flow. When the therapeutic substance comprises embolic beads, this can advantageously prevent reflux of the embolic beads, which can be dangerous.

15 Claims, 8 Drawing Sheets

(51) Int. Cl.
   *A61M 39/22* (2006.01)
   *A61M 39/10* (2006.01)
(52) U.S. Cl.
   CPC .... *A61M 5/16854* (2013.01); *A61M 5/16881* (2013.01); *A61M 39/22* (2013.01); *A61M 2039/1083* (2013.01); *A61M 2039/226* (2013.01); *A61M 2205/3317* (2013.01); *A61M 2205/3331* (2013.01); *A61M 2205/502* (2013.01); *A61M 2206/11* (2013.01)
(58) Field of Classification Search
   CPC .... A61M 2039/226; A61M 2205/3331; A61M 2205/502; A61M 2206/11; A61M 5/14228; A61M 5/007; A61M 5/16809; A61B 17/12186
   See application file for complete search history.

(56) References Cited

U.S. PATENT DOCUMENTS

| | | | |
|---|---|---|---|
| 10,039,551 | B2 | 8/2018 | Kipshidze et al. |
| 2007/0197963 | A1 | 8/2007 | Griffiths et al. |
| 2012/0016299 | A1* | 1/2012 | Caffey .............. A61M 5/14276 |
| | | | 604/151 |
| 2015/0133780 | A1 | 5/2015 | Kipshidze et al. |
| 2015/0335453 | A1 | 11/2015 | Kipshidze et al. |
| 2016/0310920 | A1* | 10/2016 | Brown ...................... B65B 3/12 |
| 2017/0319770 | A1 | 11/2017 | Fitzgerald et al. |
| 2018/0168661 | A1 | 6/2018 | Kipshidze et al. |
| 2018/0296225 | A1 | 10/2018 | Kipshidze et al. |
| 2019/0262524 | A1* | 8/2019 | Wyeth ................. A61M 1/1674 |
| 2020/0268670 | A1 | 8/2020 | Kipshidze et al. |

* cited by examiner

FIG. 5A

WHAT DO YOU WANT TO DO NEXT?

[INJECT SALINE] [INJECT CONTRAST] [INJECT BEADS]

[END THE PROCEDURE]

SALINE INJECTION

[SELECT VOLUME] [SELECT FLOW RATE]

PRESS RED BUTTON TO START INJECTION

[CANCEL]

CONTRAST INJECTION

[SELECT VOLUME] [SELECT FLOW RATE]

PRESS RED BUTTON TO START INJECTION

[CANCEL]

BEADS INJECTION

[SELECT VOLUME]

PRESS RED BUTTON TO START INJECTION

[CANCEL]

— 15T

DUAL-PUMP SYSTEM FOR DELIVERING EMBOLIC BEADS OR OTHER THERAPEUTIC SUBSTANCES INTO AN ARTERY

BACKGROUND

U.S. Pat. No. 9,572,700, which is incorporated herein by reference in its entirety, describes a treatment for obesity by selectively delivering embolic particles into the distal portion of the left gastric artery via a catheter. And US Patent Application Publication 2018/0168661, which is incorporated herein by reference in its entirety, describes an automated system that controls the delivery of embolic beads into a subject's artery.

SUMMARY OF THE INVENTION

One aspect of the invention is directed to a first apparatus for controlling delivery of a suspension of a therapeutic substance dispersed within a liquid. The first apparatus comprises a first inlet port, a second inlet port, at least one valve, an outlet port, a first pump, a fluid tight reservoir, a bidirectional pump, a first actuator, and a controller. The at least one valve is arranged to selectively open or close a first fluid-flow path between the first inlet port and a central fluid path and to selectively open or close a second fluid-flow path between the second inlet port and the central fluid path. The first pump has an inlet in fluid communication with the central fluid path and an outlet in fluid communication with the outlet port. The first pump is configured to, when actuated, pump liquid from the central fluid path to the outlet port at a first flow rate. The bidirectional pump has a first orifice in fluid communication with the central fluid path and a second orifice in fluid communication with the reservoir. The bidirectional pump is configured to, when actuated in a first mode, pump liquid from the first orifice to the second orifice at a flow rate that is at least double the first flow rate. The bidirectional pump is also configured to, when actuated in a second mode, pump liquid from the second orifice to the first orifice. The first actuator is configured to, in response to a state of at least one control input, control the at least one valve. The controller is configured to (i) control the state of the at least one control input, (ii) control the state of a first signal that actuates the first pump, and (iii) control the state of at least one second signal that actuates the bidirectional pump in either the first mode or the second mode.

Some embodiments of the first apparatus further comprise an additional valve arranged to selectively open or close a fluid-flow path between the second orifice of the bidirectional pump and the outlet of the first pump, and an additional actuator configured to, in response to a state of an additional control input, selectively open or close the additional valve. In these embodiments, the controller is further configured to control the state of the additional control input.

Some embodiments of the first apparatus further comprise an additional valve arranged to selectively open or close a fluid-flow path between the second orifice of the bidirectional pump and the outlet of the first pump, and an additional actuator configured to, in response to a state of an additional control input, selectively open or close the additional valve. These embodiments further comprise a third inlet port. In these embodiments, the at least one valve is further arranged to selectively open or close a third fluid-flow path between the third inlet port and the central fluid path. The first pump comprises a peristaltic pump and the bidirectional pump comprises a peristaltic pump. The first fluid-flow path comprises tubing that runs between the first inlet port and the central fluid path, and the at least one valve comprises a first pinch valve arranged to selectively open or close the first fluid-flow path. The second fluid-flow path comprises tubing that runs between the second inlet port and the central fluid path, and the at least one valve further comprises a second pinch valve arranged to selectively open or close the second fluid-flow path. The third fluid-flow path comprises tubing that runs between the third inlet port and the central fluid path, and the at least one valve comprises a third pinch valve arranged to selectively open or close the third fluid-flow path. In these embodiments, the controller is further configured to control the state of the additional control input. Optionally, in these embodiments, the first actuator comprises a first cam positioned to selectively open or close the first pinch valve, a second cam positioned to selectively open or close the second pinch valve, and a third cam positioned to selectively open or close the third pinch valve.

Optionally, the embodiments described in the previous paragraph further comprise a first pressure sensor and a conductivity sensor. The first pressure sensor is positioned to measure pressure in the central fluid path, and output data indicative of a measured pressure. The conductivity sensor is positioned to measure conductivity in a fluid-flow line that leads to the outlet port and output data indicative of the measured conductivity. The controller is further configured to accept the data output by the first pressure sensor and to accept the data output by the conductivity sensor. Optionally, in these embodiments, the first inlet port comprises a female Luer inlet, the second inlet port comprises a female Luer inlet, the third inlet port comprises a female Luer inlet, and the outlet port comprises a male Luer outlet.

In some embodiments of the first apparatus, when actuated in the first mode, the bidirectional pump pumps liquid from the first orifice to the second orifice at a flow rate that is at least five times the first flow rate. In some embodiments of the first apparatus, when actuated in the first mode, the bidirectional pump pumps liquid from the first orifice to the second orifice at a flow rate greater than 30 cc/min, and the first flow rate is less than 10 cc/min.

Some embodiments of the first apparatus further comprise a first pressure sensor positioned to measure pressure in the central fluid path. The first pressure sensor outputs data indicative of a measured pressure, and the controller is further configured to accept the data output by the first pressure sensor.

Some embodiments of the first apparatus further comprise a first pressure sensor positioned to measure pressure in the central fluid path. The first pressure sensor outputs data indicative of a measured pressure. In these embodiments, the controller is further configured (1) to accept the data output by the first pressure sensor, and (2) to determine a flow rate by tracking at least one of transitions, peaks, and troughs in the data output by the first pressure sensor.

Some embodiments of the first apparatus further comprise a first pressure sensor positioned to measure pressure in the central fluid path. The first pressure sensor outputs data indicative of a measured pressure. In these embodiments, the controller is further configured (1) to accept the data output by the first pressure sensor, and (2) to determine a flow volume by tracking at least one of transitions, peaks, and troughs in the data output by the first pressure sensor.

Some embodiments of the first apparatus further comprise a first pressure sensor positioned to measure pressure in the central fluid path. The first pressure sensor outputs data indicative of a measured pressure. In these embodiments, the controller is further configured (1) to accept the data output by the first pressure sensor, and (2) to control the state of the at least one second signal that actuates the bidirectional pump based on the data output by the first pressure sensor so that (a) the bidirectional pump pumps a first quantity of liquid from the first inlet port to the reservoir until a large rise in pressure occurs, and (b) the bidirectional pump subsequently pumps a second, smaller, quantity of liquid from the reservoir to the first inlet port.

Some embodiments of the first apparatus further comprise a first pressure sensor positioned to measure pressure in the central fluid path. The first pressure sensor outputs data indicative of a measured pressure. These embodiments further comprise a catheter configured to mate with the outlet port. The catheter includes a second pressure sensor positioned at a distal end of the catheter, and the second pressure sensor outputs data indicative of a measured pressure. In these embodiments, the controller is further configured to accept the data output by the first pressure sensor and to accept the data output by the second pressure sensor. Optionally, in these embodiments, the controller is also further configured to control the state of the first signal so as to adjust a pumping rate of the first pump based on the data output by the first pressure sensor and the data output by the second pressure sensor.

Some embodiments of the first apparatus further comprise a first pressure sensor positioned to measure pressure in the central fluid path. The first pressure sensor outputs data indicative of a measured pressure. These embodiments further comprise a catheter configured to mate with the outlet port. The catheter includes a second pressure sensor positioned at a distal end of the catheter, and the second pressure sensor outputs data indicative of a measured pressure. In these embodiments, the controller is further configured (1) to accept the data output by the first pressure sensor; (2) to accept the data output by the second pressure sensor; and (3) to control the state of the first signal so as to increase a pumping rate of the first pump if a pressure measured by the second pressure sensor exceeds a pressure measured by the first pressure sensor.

In some embodiments of the first apparatus, the first inlet port, the second inlet port, the at least one valve, the outlet port, the first pump, and the bidirectional pump are housed by a housing. The housing has a base. In these embodiments, the first inlet port is positioned with respect to the housing so that when the base rests on a horizontal surface and a syringe is mated with the first inlet port, the syringe will be oriented vertically with respect to the horizontal surface, plus or minus 30°.

In some embodiments of the first apparatus, the first inlet port, the second inlet port, the at least one valve, the outlet port, the first pump, and the bidirectional pump are housed by a housing that has a base. The first inlet port is positioned with respect to the housing so that when the base rests on a horizontal surface and a syringe is mated with the first inlet port, the syringe will be oriented vertically with respect to the horizontal surface, plus or minus 15°.

In some embodiments of the first apparatus, the controller is further configured to control the state of the first signal that actuates the first pump so that when the first pump is used to pump a liquid through a catheter that has been connected to the outlet port, the liquid exiting the catheter has a laminar flow.

Some embodiments of the first apparatus further comprise a first pressure sensor and a user interface. The first pressure sensor is positioned to measure pressure in the central fluid path, and to output data indicative of the measured pressure. The user interface is configured to generate an output signal in response to user input. In these embodiments, the controller is further configured to accept the data output by the first pressure sensor. The controller is also configured to, in response to the output signal generated by the user interface: (1) control the state of the at least one control input so that the first actuator controls the at least one valve so that the at least one valve opens the first fluid-flow path and closes the second fluid-flow path; (2) subsequently control the state of the at least one second signal that actuates the bidirectional pump based on the data output by the first pressure sensor so that the bidirectional pump pumps a first quantity of liquid from the first inlet port to the reservoir until the data indicative of the measured pressure reveals a large rise in pressure; (3) subsequently control the state of the at least one second signal that actuates the bidirectional pump so that the bidirectional pump pumps a second quantity of liquid from the reservoir to the first inlet port, wherein the second quantity is smaller than the first quantity; and (4) subsequently control the state of the first signal that actuates the first pump so that the first pump pumps liquid from the first inlet port to the outlet port.

BRIEF DESCRIPTION OF THE DRAWINGS

FIGS. 5A-5D depict four different states of a touchscreen-based user interface that is used in some embodiments.

Various embodiments are described in detail below with reference to the accompanying drawings, wherein like reference numerals represent like elements.

DESCRIPTION OF THE PREFERRED EMBODIMENTS

Although the system described in US 2018/0168661 provides a significant degree of control over the delivery of embolic beads, the inventors have recognized a need to provide more precise control over the delivery of embolic beads. When more precise control is provided, it becomes easier to deliver a precise desired quantity of embolic beads into the target artery. Improving the precision of the delivery of embolic beads is advantageous because when too few embolic beads are delivered, the target artery may not be blocked properly. And when too many embolic beads are delivered, those beads can reflux and travel to non-target portions of the subject's vasculature, which can be problematic.

Figure 1:
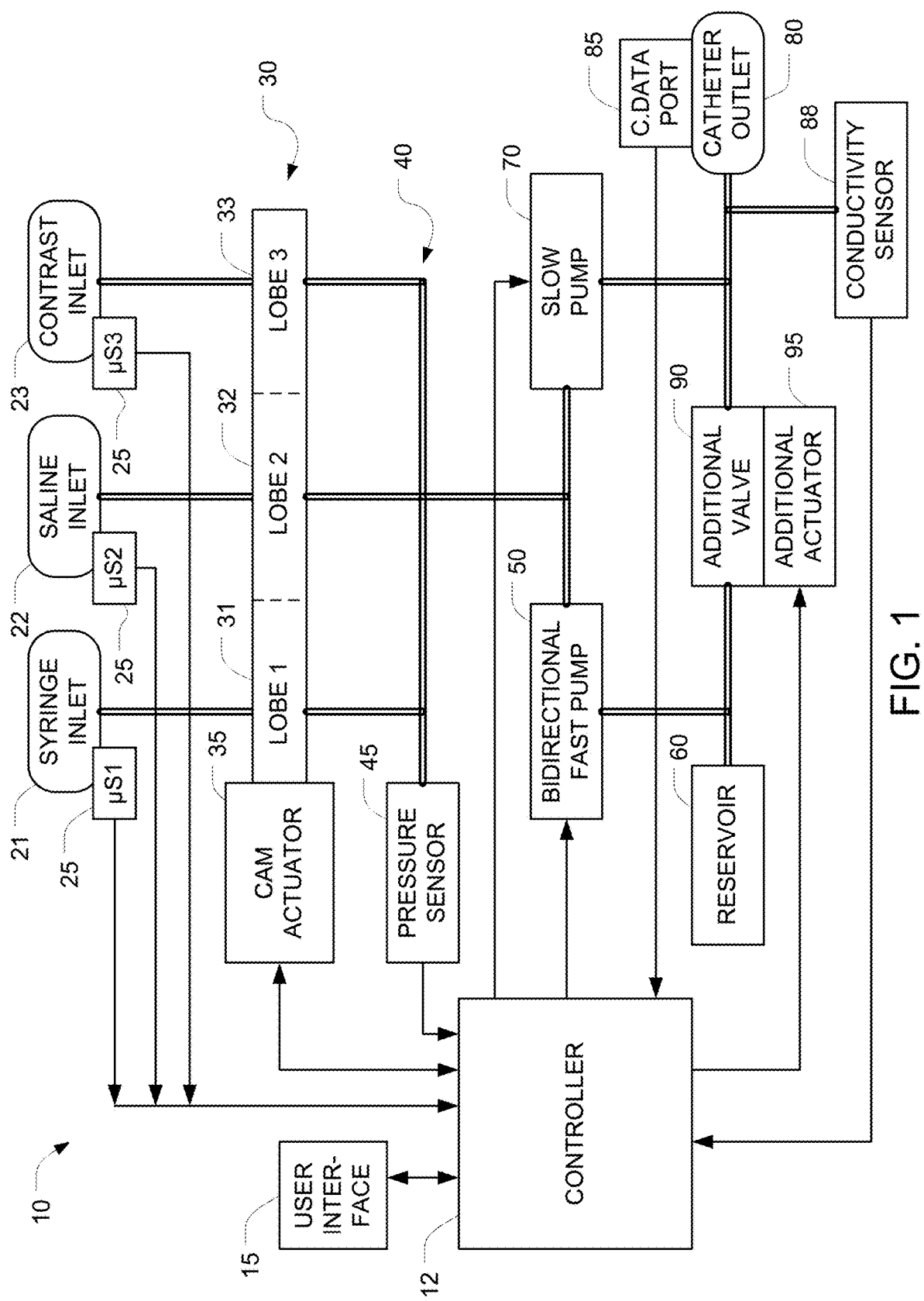
FIG. 1 is a block diagram of an embodiment for controlling the delivery of embolic beads into a subject's artery via a lumen of a catheter.

FIG. 1 is a block diagram of an apparatus 10 for controlling the delivery of embolic beads into a subject's artery via a lumen of a catheter. Note that fluid flow paths in FIG. 1 are indicated using double lines, while electrical signals and data flow paths are indicated using single lines. One possible use for this apparatus 10 is to deliver embolic beads to the distal portion of a subject's left gastric artery in order to achieve a reduction in the production of Ghrelin. A wide variety of alternative uses are also possible in different portions of a subject's vasculature.

In some preferred embodiments, the apparatus 10 is a single-use, disposable device that is powered by internal batteries (not shown). The apparatus 10 automatically controls the delivery of embolic beads and fluid through a catheter 100 (shown in FIG. 2) that is connected to the catheter outlet 80.

The controller 12 orchestrates the operation of the entire apparatus 10. It accomplishes this by sending control signals to the various components described below and receiving status signals from the various components described below. The controller 12 may be implemented using a microprocessor or a microcontroller that is programmed to implement the sequences of steps described below. The controller 12 has access to sufficient RAM and nonvolatile memory such as ROM, SSD, etc. (not shown). In alternative embodiments (not shown) the controller 12 may be implemented using microprogrammed or hardwired logic.

Figure 4D:
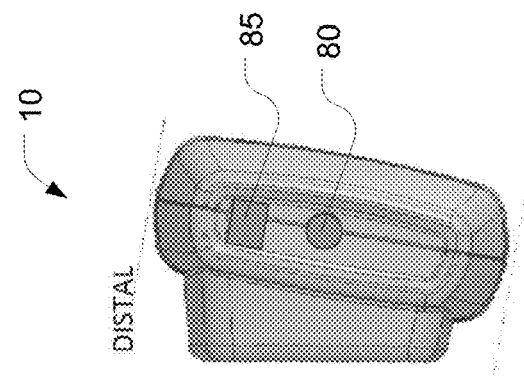
Figure 4B:
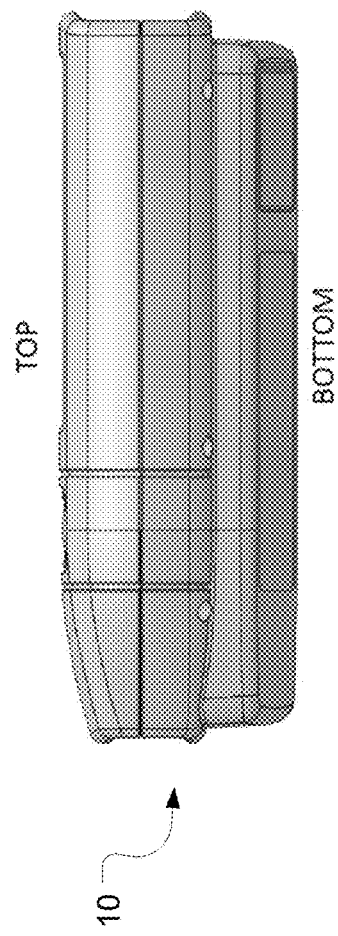
Figure 4A:
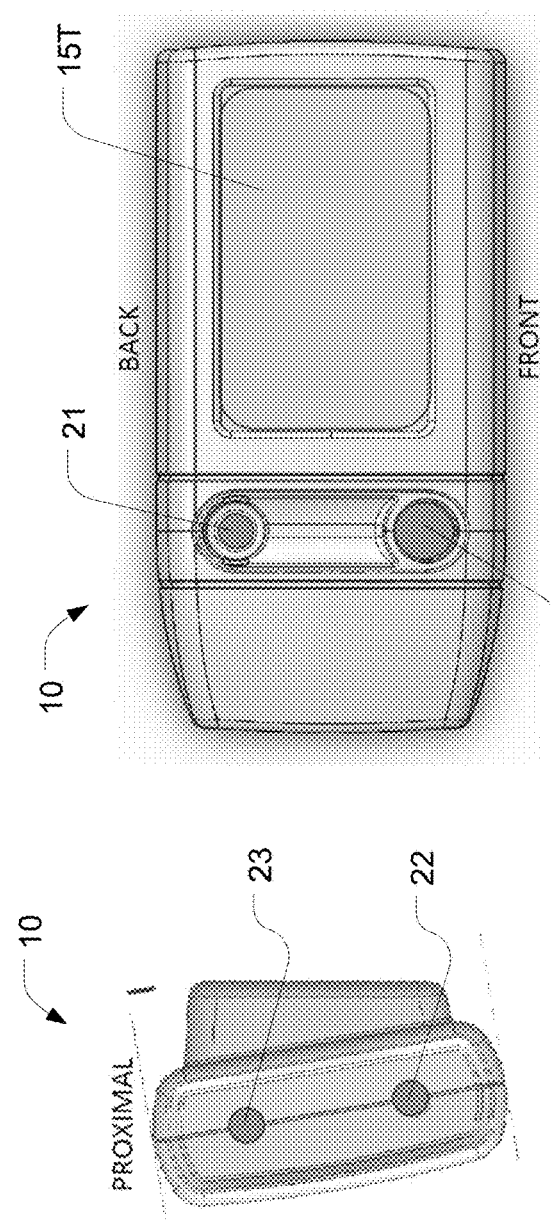
Figure 4C:
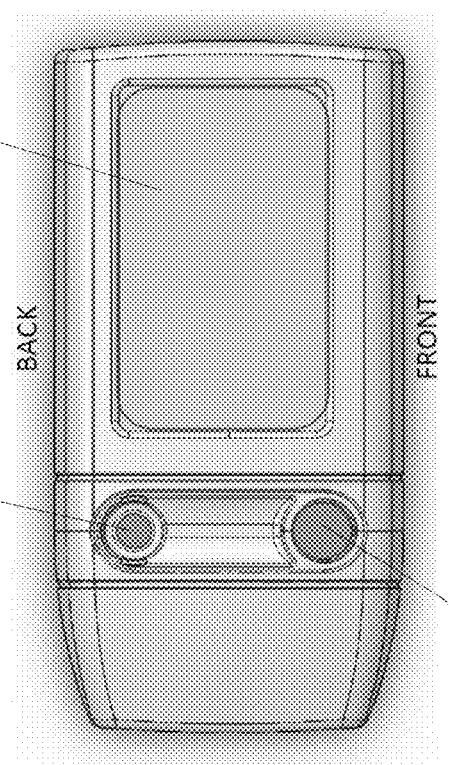

A user interface 15 allows the controller 12 to communicate with the user. In some embodiments, the user interface 15 includes a "start" button 15B and a touchscreen 15T (both depicted in FIG. 4A). Of course, this combination of a start button and touchscreen is only one example of a user interface that is suitable for the purposes described herein, and a wide variety of alternative suitable user interfaces will be apparent to persons skilled in the relevant arts.

Figure 4E:
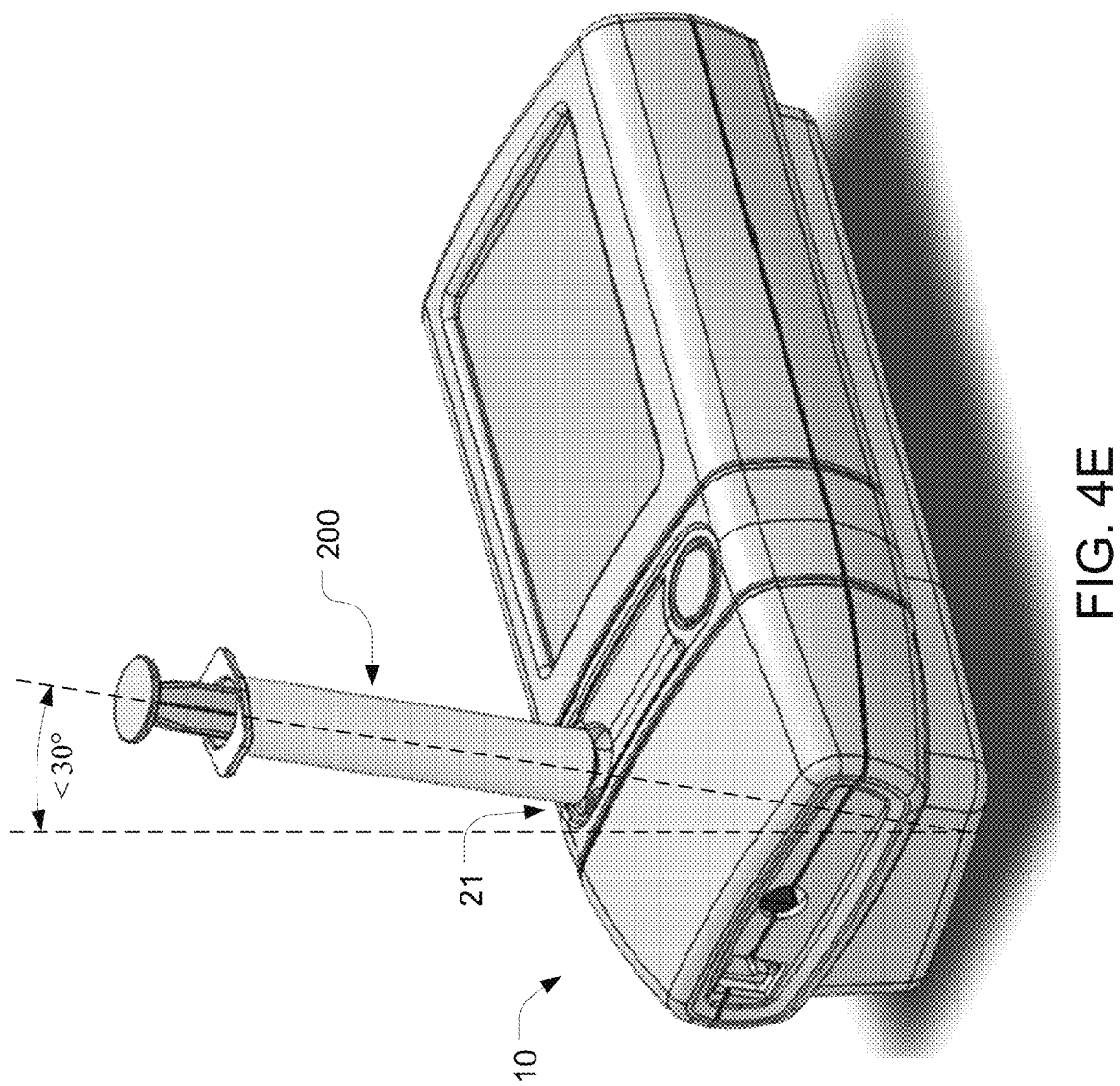

The apparatus 10 includes a first inlet port 21 (also referred to herein as a syringe inlet port) configured to provide a fluid-tight coupling with an orifice of an external syringe when an external syringe is connected to the first inlet port. During use, a syringe 200 containing embolic beads mixed in a liquid will be connected to the first inlet port 21 (as depicted in FIG. 4E). The mixture of embolic beads in the liquid is sometimes referred to herein as the "therapeutic agent." In some embodiments, the first inlet port 21 is a female Luer inlet that interfaces with the external syringe using a Luer lock coupling. Optionally, the Luer lock coupling may be disposed at the bottom of a well-shaped cavity that is shaped to accept the external syringe (e.g. a 10 cc syringe).

A second inlet port 22 (also referred to herein as a saline inlet port) is arranged to provide a fluid-tight coupling with a source of saline solution. During use, a source of saline solution (e.g., an infusion bag filled with saline) will be connected to the second inlet port 22. In some embodiments, the second inlet port 22 is a female Luer inlet.

In the FIG. 1 embodiment, a third inlet port 23 (also referred to herein as a contrast inlet port) is arranged to provide a fluid-tight coupling with a source of contrast agent. In these embodiments, a source of contrast agent will be connected to the third inlet port 23 during use. In some embodiments, the source of contrast agent could be a syringe or infusion bag that is filled with the contrast agent, in which case a Luer coupling that is similar to the first inlet port 21 may be used to implement the third inlet port 23. In alternative embodiments, the third inlet port 23 may be omitted. But in these embodiments, contrast will not be available.

In the FIG. 1 embodiment, each of the inlet ports 21-23 has an associated microswitch 25 that is mechanically configured so that the microswitch actuates when a connection to the inlet port is made. An output of each of the microswitches 25 is provided to the controller 12. This feature is used to inform the controller 12 that a connection has been made to one or more of the inlet ports 21-23. Note that in some embodiments, the microswitches 25 may be omitted.

At least one valve 30 is arranged to selectively open or close a first fluid-flow path between the first inlet port 21 and a central fluid path 40 and to selectively open or close a second fluid-flow path between the second inlet port 22 and the central fluid path 40. And in those embodiments that include the third inlet port 23, the at least one valve 30 is further arranged to selectively open or close a third fluid-flow path between the third inlet port 23 and the central fluid path 40.

A first actuator 35 controls the at least one valve 30 to switch between a number of states in response to a state of at least one control input. The controller 12 controls the first actuator 35 by issuing control commands that control the state of the at least one control input. In response to a first state of the at least one control input, the first actuator 35 moves the at least one valve 30 to a position that opens the fluid flow path between the first inlet port 21 and the central fluid path 40, and closes the fluid flow paths between the central fluid path 40 and the other inlet ports 22, 23. In response to a second state of the at least one control input, the first actuator 35 moves the at least one valve 30 to a position that opens the fluid flow path between the second inlet port 22 and the central fluid path 40, and closes the fluid flow paths between the central fluid path 40 and the other inlet ports 21, 23. In response to a third state of the at least one control input, the first actuator 35 moves the at least one valve 30 to a position that opens the fluid flow path between the third inlet port 23 and the central fluid path 40, and closes the fluid flow paths between the central fluid path 40 and the other inlet ports 21, 22. In response to a fourth state of the at least one control input, the first actuator 35 moves the at least one valve 30 to a position that opens the fluid flow paths between the central fluid path 40 and each of the inlet ports 21-23. And in response to a fifth state of the at least one control input, the first actuator 35 moves the at least one valve 30 to a position that closes all the fluid flow paths between the central fluid path 40 and the inlet ports 21-23.

The first actuator 35 will include a component that converts electromagnetic energy into motion (e.g., a DC motor, a stepper motor, a linear actuator, etc.) to move the at least one valve 30 to the desired position. The first actuator 35 also includes a driver circuit (not shown) configured to generate whatever signals are needed to drive that component and make it respond to the low-level signals that arrive from the controller 12. Details of the implementation of the driver circuit for the first actuator 35 will depend on the nature of the moving component, and will be apparent to persons skilled in the relevant arts.

A variety of formats for the low-level signals that are applied to the driver circuit can be readily envisioned. In one example, the controller 12 can initiate the first through fifth states by writing specific control words to one or more memory mapped control addresses. In another example, the controller could have five dedicated output lines that, when asserted, respectively cause the first actuator 35 to move to a corresponding position. A variety of alternative approaches will be apparent to persons skilled in the relevant arts Optionally, the first actuator 35 may include one or more sensors that can be used to report its current status back to the controller 12. Examples of suitable sensors for this purpose include optical encoders, magnetic encoders, resolvers, a plate connected to a sliding shaft with slots that either permit light to travel between an emitter and a photodetector block or block that light, etc. If, at any time, feedback from the sensors indicates that the first actuator 35 has not switched to a desired state in response to a command, the controller 12 can take appropriate action to try to get the first actuator 35 to move to the desired state (e.g., re-issuing an appropriate control signal, requesting additional rotation, etc.).

In some embodiments (including the embodiment depicted in FIG. 1), each of the fluid flow paths between the first, second, and third inlet ports 21-23 and the central fluid path 40 is implemented using a segment of medical-grade flexible tubing that runs between the inlet ports 21-23 and the central fluid path 40, and each of those segments of flexible tubing is selectively either opened or closed by a corresponding one of three cams (31-33) that either presses against the segment of flexible tubing (to close a given segment) or does not press against the segment of flexible tubing (to leave a given segment open). The interaction between these cams 31-33 and the segments of flexible tubing therefore operate as pinch valves. Suitable materials for the flexible tubing include silicone and other biocompatible elastomers or elastomerics. In these embodiments, the first actuator 35 is a cam actuator that moves each of the three cam lobes 31-33 to a position that implement a desired one of the five states identified above, in response to a corresponding one of the five states of the at least one control input.

In alternative embodiments (not shown), the at least one valve 30 may be implemented using a different approach, including but not limited to using a rotary valve that has three input ports and a single output port. In this case, each of the first, second, and third inlet ports 21-23 would be connected to a corresponding one of the rotary valve's three input ports using appropriate tubing, and the rotary valve's output port would be connected to the central fluid path 40 using appropriate tubing. In these embodiments, in response to control commands received from the controller 12, the first actuator moves the rotary valve to either (1) a first position where the first input port is connected to the output port; (2) a second position where the second input port is connected to the output port; (3) a third position where the third input port is connected to the output port; or (4) a fourth position where all the input ports are connected to the output port. These four positions correspond to the first four states discussed above. A variety of alternative approaches for implementing the at least one valve 30 will be apparent to persons skilled in the relevant arts.

The apparatus 10 also includes an outlet port 80 configured to provide a fluid-tight connection with the lumen of the catheter 100 (shown in FIG. 2) when the catheter is connected to the outlet port. In some embodiments, the outlet port 80 is a male Luer outlet.

Figure 2:
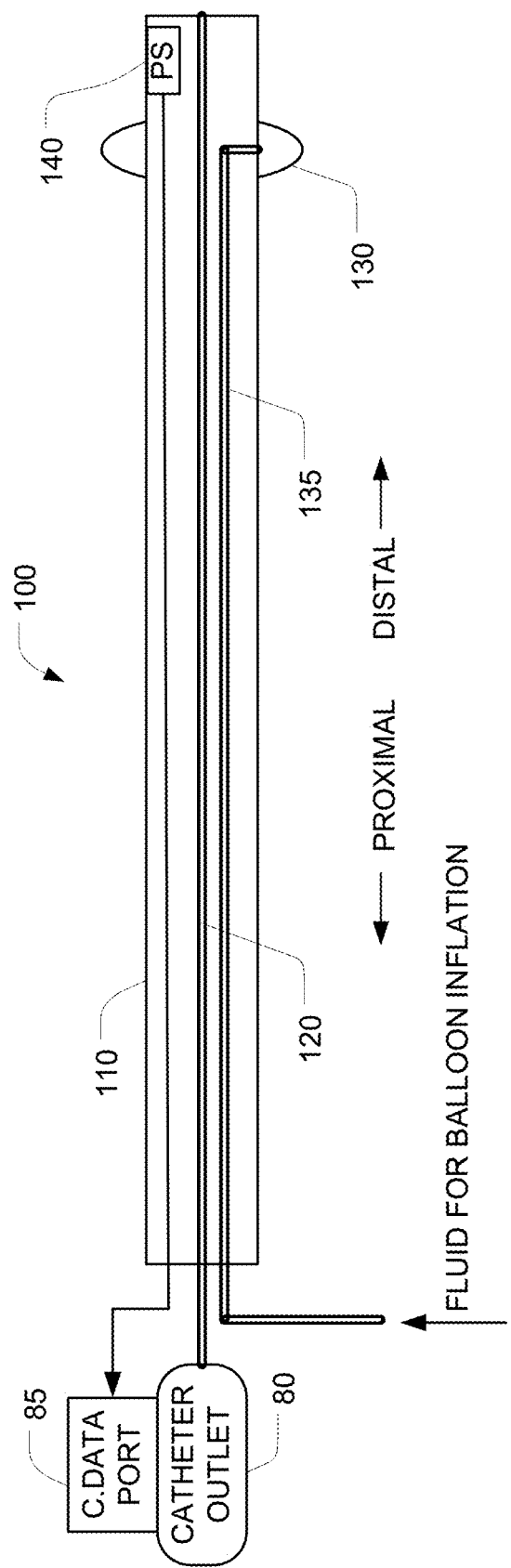
FIG. 2 depicts a catheter that is used in conjunction with the apparatus of FIG. 1.

FIG. 2 depicts a catheter 100 that is used in conjunction with the apparatus 10 (depicted in FIG. 1). The catheter 100 depicted in FIG. 2 has a catheter body 110, and a main lumen 120 runs through the catheter body 110. The proximal side of the catheter 100 mates with the catheter outlet 80 with a fluid tight coupling so that fluid exiting the catheter outlet 80 enters the main lumen 120, flows therethrough, and eventually exits the distal side of the main lumen 120. Note that is used herein, distal and proximal are oriented with respect to the practitioner who is using the device, so that distal means further away from the practitioner (and deeper into the patient's body), and proximal means closer to the practitioner. An occlusion balloon 130 is positioned near the distal end of the catheter 100, and this balloon can be inflated or deflated using a fluid that flows into and out of the occlusion balloon 130 via the balloon inflation lumen 135. A distal pressure sensor 140 is positioned at the distal end of the catheter 100, distally with respect to the occlusion balloon 130. Output signals from this distal pressure sensor 140 travel in a proximal direction through the catheter 100, until they arrive at the catheter data port 85 of the apparatus 10.

Returning to FIG. 1, the apparatus 10 includes a catheter data port 85 that accepts the data arriving from the distal pressure sensor 140. This data is routed to the controller 12, and is used as described below.

The apparatus 10 also includes a first pump 70, and this first pump 70 has an inlet in fluid communication with the central fluid path 40 and an outlet in fluid communication with the outlet port 80. The connection between the outlet of the first pump 70 in the outlet port 80 may be made, for example, using appropriate medical-grade tubing.

The first pump 70 is configured to, when actuated, pump liquid from the central fluid path 40 to the outlet port 80 at a first flow rate. Preferably, the first pump 70 is optimized to operate at relatively slow flow rates, and to provide precise control of the volume of fluid that is being pumped.

Figure 3:
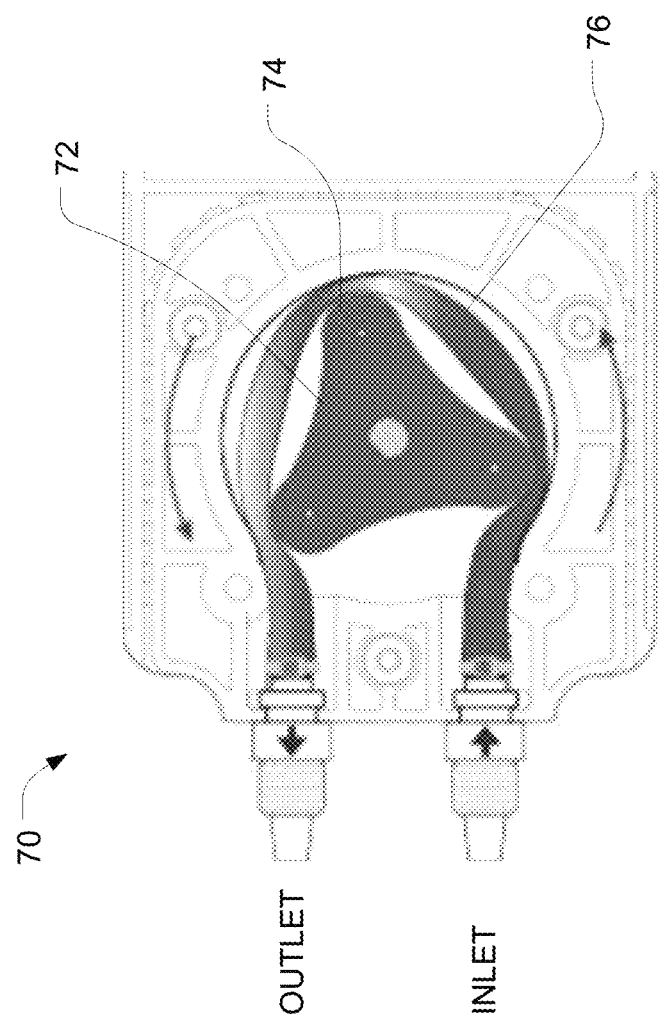
FIG. 3 depicts one preferred approach for implementing the first pump in FIG. 1 as a peristaltic pump FIGS. 4A-4E respectively depict top, front, proximal, distal, and perspective views of the FIG. 1 apparatus within a housing.

FIG. 3 depicts one preferred approach for implementing the first pump 70. In this approach, the pump 70 is a peristaltic pump. The operation of peristaltic pumps is well understood by persons skilled in the relevant arts. Briefly, when an electrical signal is applied to the pump, the rotor 72 will rotate at a speed that depends on the voltage of the applied signal. The rotation of the rotor 72 causes rollers 74 that squeeze the tubing 76 to move along the surface of the tubing 76, thereby pushing the fluid within the tubing 76 through that tubing. Preferably, in these embodiments, the flow of fluid through the tubing 76 is blocked when the rotor 72 is not rotating. Note that while FIG. 3 depicts a peristaltic pump, a variety of alternative pump architectures may be substituted therefor.

In some embodiments, the inner diameter of the pump casing is 1.349 inches, the tubing 76 has an outer diameter of 2.5 mm and an inner diameter of 0.7 mm, the rotor 72 has a diameter of 0.705 inches, the rollers 74 each have a diameter of 0.570 inches, and the gap between the rollers 74 and the casing is 0.037 inches.

Returning to FIG. 1, the controller 12 controls the state of a first signal that actuates the first pump 70. The nature of this first signal will depend on the construction of the pump 70. For example, the pump 70 may be configured to pump at a speed that is proportional to an applied DC voltage, and remain off when no voltage is applied. In these embodiments, the controller 12 could output a digital word to an analog circuit (not shown) that converts the digital word to a corresponding DC voltage; and this DC voltage is applied to the electrical terminals of the first pump 70.

The apparatus 10 also includes a fluid-tight reservoir 60 and a bidirectional pump 50 (also referred to herein as a fast pump). The bidirectional pump 50 has a first orifice in fluid communication with the central fluid path 40 and a second orifice in fluid communication with the reservoir 60. The bidirectional pump is configured to, when actuated in a first mode, pump liquid from the first orifice to the second orifice at a flow rate that is at least double the first flow rate. This will pump liquid from the central fluid path 40 into the reservoir 60. The bidirectional pump 50 is also configured to, when actuated in a second mode, pump liquid from the second orifice to the first orifice. This will pump liquid in the opposite direction, i.e., from the reservoir 60 to the central fluid path 40.

The fluid-tight reservoir 60 may be implemented using a simple syringe (e.g. a 10 cc syringe). In some embodiments, the syringe that serves as the fluid-tight reservoir 60 is the same size as the syringe that contains the embolic beads (which, as described below, will eventually be connected to the first inlet port 21).

One preferred approach for implementing the bidirectional pump 50 is to use a reversible peristaltic pump. The construction of the reversible peristaltic pump is similar to the operation of the pump 70 described above in connection with FIG. 3, except that the rotor can rotate in either direction. For example, the rotor could rotate in one direction when a positive voltage is applied to its terminals, and rotate in the opposite direction when a negative voltage is applied to its terminals, with the speed in either case being proportional to the magnitude of the voltage. In alternative embodiments, pumping technologies other than peristaltic pumps may be used to implement the bidirectional pump 50.

Preferably, the bidirectional pump 50 is optimized to operate at flow rates that are at least double the flow rate of the first pump 70. The bidirectional pump 50 is preferably optimized for speed as opposed to precision, as the need to provide precise control of the volume of fluid that is being pumped is not so critical for the bidirectional pump 50. In some embodiments, the inner diameter of the pump casing is 1.383 inches, the tubing has an outer diameter of 4.5 mm and an inner diameter of 2.5 mm, the rotor has a diameter of 0.705 inches, the rollers each have a diameter of 0.570 inches, and the gap between the rollers and the casing is 0.054 inches.

The controller 12 controls the state of at least one second signal that actuates the bidirectional pump 50 in either the first mode or the second mode. The nature of the at least one second signal will depend on the construction of the bidirectional pump 50. For example, the bidirectional pump 50 may be configured to pump in one direction at a speed that is proportional to an applied positive DC voltage, pump in the opposite direction at a speed that is proportional to an applied negative DC voltage, and remain off when no voltage is applied. In this situation, the at least one second signal could be a single digital control word. The controller 12 outputs this digital control word to an analog circuit (not shown) that converts the digital control word to a corresponding positive or negative DC voltage; and this DC voltage is applied to the electrical terminals of the bidirectional pump 50. Alternatively, the at least one second signal could comprise one signal that causes the bidirectional pump 50 to move in one direction, and a separate signal that causes the bidirectional pump 50 to move in the opposite direction.

The embodiment depicted in FIG. 1 also includes an additional valve 90 arranged to selectively open or close a fluid-flow path between the second orifice of the bidirectional pump 50 and the outlet of the first pump 70 (which, as noted above, is in fluid communication with the outlet port 80). When this additional valve 90 is open, fluid that exits the second orifice of the bidirectional pump 50 can flow through the additional valve 90 and out of the outlet port 80. But when this additional valve 90 is closed, all fluid that exits the second orifice of the bidirectional pump 50 will flow into the reservoir 60. Note that the additional valve 90 will normally be closed; and the only times that the additional valve 90 will be open are (a) when the bidirectional pump 50 is pumping a fluid out to the outlet port 80, and (b) during priming of the system.

An additional actuator 95 is configured to selectively open or close the additional valve 90 in response to a state of an additional control input. The controller 12 controls the additional actuator 95 by issuing control commands that control the state of the additional control input. More specifically, in response to one state of the additional control input, the additional actuator 95 causes the valve 90 to open the fluid-flow path between the second orifice of the bidirectional pump 50 and the outlet of the first pump 70; and in response to another state of the additional control input, the additional actuator 95 causes the valve 90 to close that fluid-flow path. Optionally, the additional actuator 95 may be configured to report its current status back to the controller 12. This optional feature is useful because it allows the controller 12 to ascertain whether the has responded properly to a previous control command that was issued by the controller 12.

In some embodiments (including the embodiment depicted in FIG. 1), the fluid-flow path between the second orifice of the bidirectional pump 50 and the outlet of the first pump 70 is implemented using flexible tubing that runs therebetween. The same type of tubing described above in connection with the at least one valve 30 may be used in these embodiments. In these embodiments, the additional actuator 95 may be implemented using a cam or solenoid that either presses against the flexible tubing (to close off the flow) or does not press against the flexible tubing (to permit flow). In alternative embodiments (not shown), the additional valve 90 and additional actuator 95 may be implemented using a different approach, the nature of which will be apparent to persons skilled in the relevant arts.

Note that while the embodiment depicted in FIG. 1 includes the additional valve 90 and the additional actuator 95, those two components may be omitted in alternative embodiments. In this situation, the bidirectional pump 50 would not have access the outlet port 80.

The FIG. 1 embodiment also includes a conductivity sensor 88 positioned to measure conductivity in the fluid-flow line that leads to the outlet port 80. This conductivity sensor 88 outputs data indicative of a measured conductivity, and this data is provided to the controller 12. The controller 12 is configured to accept the data output by the conductivity sensor 88.

The FIG. 1 embodiment also includes a first pressure sensor 45 positioned to measure pressure in the central fluid path 40. The first pressure sensor 45 outputs data indicative of a measured pressure, and this data is provided to the controller 12. The controller 12 is configured to accept the data output by the first pressure sensor 45, and the controller 12 uses this data to determine how many rotations the pumps 50, 70 are making.

More specifically, as noted above, in some embodiments the first pump 70 and the bidirectional pump 50 are peristaltic pumps. In these embodiments, when a roller in either pump 50, 70 engages the tube, it will induce a pressure peak; and when a roller in either pump 50, 70 lifts off the tube, it will induce a pressure dip. The first pressure sensor 45 detects these pressure variations and reports them to the controller 12. When a peristaltic pump is implement using three rollers (as depicted in FIG. 3), three peaks and three valleys will correspond to one revolution of the pump's rotor. The pressure information from the first pressure sensor 45 can therefore be translated to pump-rotor revolution information by the controller 12. The controller 12 can do this based on at least one of transitions, peaks, and troughs in the data output by the first pressure sensor 45. Notably, using pressure information to encode rotation advantageously eliminates the need for other type of feedback from the pumps (e.g., optical encoders, synchros, resolvers, etc.), thereby simplifying the design, increasing reliability, and reducing cost.

Each time a roller in a peristaltic pump passes over the tubing, a fluid bolus is pushed out of the pump's outlet tubing. Knowing the bolus volume and number of pressure peaks, the controller 12 can determine the volume of fluid that is being pumped by either one of the pumps 50, 70. The controller 12 can also determine a flow rate by dividing that volume by time.

FIGS. 4A-4D depict top, front, proximal, and distal views of the apparatus 10 when that apparatus is implemented within a housing. And FIG. 4E depicts a perspective view of the same apparatus 10. In the view depicted in FIG. 4E, the syringe 200 (which contains embolic beads mixed in a liquid) is connected to the first inlet port 21. The first inlet port 21 is positioned with respect to the housing so that when the base rests on a horizontal surface and a syringe 200 is mated with the first inlet port 21, the syringe will be oriented vertically with respect to the horizontal surface, plus or minus 30°. In some preferred embodiments, the syringe will be oriented vertically with respect to the horizontal surface, plus or minus 15°. The significance of this substantially vertical orientation of the syringe 200 will be explained below.

Having described the various hardware components and the interconnections therebetween, we shall next describe an example how the apparatus 10 can be used in a procedure for delivering a precise desired quantity of embolic beads into a target artery of a living subject.

Operating Procedure: The procedure for delivering a quantity of embolic beads into a target artery includes three distinct phases. The first phase is the PRIMING phase, where the fluid flow pathways within the apparatus 10 are flushed with saline. This phase is important to prevent the introduction of bubbles into the subject's bloodstream. The second phase is the CONNECTION phase, during which the syringe 200 that contains the embolic beads, the catheter 100, and a source of contrast agent are connected to the apparatus 10. The third phase is the INJECTION phase, during which at least one of the embolic beads, the saline, and the contrast agent is pumped out into the catheter 100 via the outlet port 80. Notably, the injection phase will typically include a sequence of two or more injections involving these three materials. For example, the injection phase could include the following sequence of six injections: (1) pump saline into the catheter; (2) pump contrast agent into the catheter; (3) pump saline into the catheter; (4) pump contrast agent into the catheter; (5) pump saline into the catheter; and (6) pump the embolic beads into the catheter.

The Priming Phase: One example of a suitable sequence of steps for implementing the priming phase is as follows:

Upon powering up, the controller 12 executes an initialization routine.

The controller 12 issues a command instructing the user interface 15 (e.g., touchscreen 15T) to prompt the user to connect a source of saline to the second inlet port 22.

The controller 12 then waits for a signal from the microswitch 25 associated with the second inlet port 22 indicating that a connection to the second inlet port 22 has been made.

The controller 12 issues a command instructing the user interface 15 to display a request for confirmation that the saline has been connected and that it is OK to start priming.

The controller 12 waits for a "start priming" command to arrive via the user interface 15 (e.g., via the button 15B, the touchscreen 15T, or an alternative user interface).

The controller 12 sets the at least one control input to the fourth state. This causes the first actuator 35 to move the at least one valve 30 to a position where all three cam lobes 31-33 open the fluid flow paths between the central fluid path 40 and each of the inlet ports 21-23.

When the first actuator 35 reports that it has moved to the appropriate position, the controller 12 stops the movement of the cam lobes 31-33 of the at least one valve 30.

Because the fluid flow path between the central fluid path 40 and each of the three inlet ports 21-23 are all open, hydrostatic pressure will cause saline to enter the saline inlet and subsequently flow into the central fluid path 40 (assuming that the source of saline is elevated with respect to all three inlet ports 21-23). From there, the saline will continue to flow out through the first inlet port 21 and the third inlet port 23.

The controller 12 then sets the at least one control input to the second state. This causes the first actuator 35 to move the at least one valve 30 so that cam lobes 31 and 33 closed the corresponding fluid flow paths, and only the path controlled by cam lobe 32 is open.

The controller 12 then controls the first signal to actuate the first pump 70. The first pump 70 will then draw saline in from the central fluid path 40 and pump it out through the catheter outlet 80. Meanwhile, replacement saline flows into the central fluid path 40 via the second inlet port 22.

The controller 12 then commands the additional actuator 95 to open the additional valve 90 and controls the at least one second signal to actuate the bidirectional pump 50 so that the bidirectional pump 50 pumps saline from the central fluid path 40 in through the first orifice of the bidirectional pump 50 and out through its second orifice. This saline will flow out through the catheter outlet 80 while replacement saline flows into the central fluid path 40 via the second inlet port 22.

The conductivity sensor 88 will detect that saline is passing out of the catheter output 80 and report this back to the controller 12. Based on this information, the controller 12 can determine that the priming phase is complete. Alternatively, the controller 12 can instruct the user interface 15 to display a message asking the user to confirm that saline has indeed exited the catheter port 80. If the controller 12 receives confirmation that this is the case from the user interface 15, the controller 12 can determine that the priming phase is complete.

If the controller 12 does not receive confirmation that saline has indeed exited the catheter port 80, the controller can return to the point in the procedure where it first actuated the first pump 70, and repeat the subsequent steps.

Once the controller 12 determines that the priming phase is complete, the controller 12 stops both the first pump 70 and the bidirectional pump 50 by generating the corresponding first signal and the corresponding at least one second signal, and closes the additional valve 90 by sending an appropriate signal to the additional actuator 95.

The Connection Phase: After the priming phase is complete, the syringe 200 (which contains embolic beads mixed in a liquid), the source of contrast agent, and the catheter 100 can be connected to the apparatus 10 in the connection phase. One example of a suitable sequence of steps for implementing the connection phase is as follows:

The controller 12 issues a command instructing the user interface 15 (e.g., touchscreen 15T) to prompt the user to connect a syringe containing embolic beads to the first inlet port 21 and to connect a source of contrast agent to the third inlet port 23.

The controller 12 then waits for a signal from the microswitches 25 associated with the first inlet port 21 and the third inlet port 23 indicating that the connections to those inlets have been made. The controller 12 then issues a command instructing the user interface 15 to display a confirmation that the syringe and the contrast have been connected.

The controller 12 issues a command instructing the user interface 15 to prompt the user to connect the fluid connector of the catheter 100 to the catheter outlet 80 and to connect the data connector of the catheter 100 to the catheter data port 85.

The controller 12 then waits for a signal from the catheter data port 85 indicating that the catheter 100 has been connected. The controller 12 then issues a command instructing the user interface 15 to display a confirmation that the catheter has been connected.

The controller 12 determines the length of the catheter based on data that arrives via the catheter data port. This could be accomplished, for example, by reading the value of a resistor (not shown) embedded within the catheter 100. Alternatively, it could be accomplished by reading the value of a data register (not shown) embedded within the catheter 100.

Optionally, the controller 12 issues a command instructing the user interface 15 to display a pressure reading based on data obtained from the distal pressure sensor 140. When the user interface 15 is implemented using a touchscreen 15 T, this could be accomplished by generating a window on the touchscreen, and displaying the pressure reading within that window.

The Injection Phase: After the connection phase is complete, the apparatus 10 is used to inject the embolic beads, the saline, and the contrast agent in the injection phase. The sequence of the injections of these three substances and the injection volume that is used for each injection is preferably controllable by the operator via the user interface 15. In some embodiments, the operator has complete control over the sequence of injections of these three substances. Typically, the injection phase will include at least one injection of saline, at least one injection of contrast agent, and at least one injection of embolic beads.

FIGS. 5A-5D depict one example of a suitable touchscreen-based user interface for those embodiments in which the operator has complete control over the sequence of injections of all three substances. This user interface relies on the touchscreen 15T to control the injection phase. The controller 12 controls the presentation of the various touchscreens 15T described herein, and accepts user inputs from the touchscreen 15T and from the button 15B. (Note that in alternative embodiments, the operator may only be provided with limited control over the sequence of injections of the three substances. The user interface screens for these embodiments will vary from the interface screens described herein depending on the nature of the limited control that is provided to the operator.)

FIG. 5A depicts an example of a suitable home screen of the user interface for implementing the injection phase. This screen provides the operator with the option to select one of four options for what they want to do next. These options include injecting saline, injecting contrast, injecting the embolic beads, and ending the procedure. The operator selects a desired option based on the circumstances of the medical procedure that is being performed.

Injecting Saline: If the operator wants to inject saline when the home screen is visible, the operator presses the "inject saline" button on the touchscreen 15T. Based on instructions from the controller 12, the touchscreen 15T will switch to the state depicted in FIG. 5B, which asks the operator to specify the volume and/or flow rate for the saline injection. Additional screens of the user interface (not shown) are presented to the operator so that the operator can set the volume and/or flow rate to the desired level. After the operator has specified the desired parameters, the operator presses the button 15B to initiate injection of the saline. The controller 12 recognizes that the button 15B has been pressed, and initiates the following sequence for injecting the saline.

First, the controller 12 sets the at least one control input to the second state. This causes the first actuator 35 to move the at least one valve 30 to a position where cam lobe 32 opens the fluid flow path between the central fluid path 40 and the second inlet port 22. The remaining lobes of the cam 31, 33 close the fluid flow paths between the central fluid path and the other inlet ports 21, 23.

When the first actuator 35 reports that it has moved to the appropriate position, the controller 12 stops movement of the first actuator 35.

The controller 12 sends a signal to the additional actuator 95 so that the additional actuator 95 opens the additional valve 90. Then, the controller 12 issues an appropriate second signal to actuate the bidirectional pump 50 in its first mode so that it pumps saline from its first orifice to its second orifice. Because the additional valve 90 is opened, the saline exiting the bidirectional pump 50 will flow through the additional valve 90 and subsequently flow out through the catheter outlet 80. Meanwhile, replacement saline flows into the central fluid path 40 via the second inlet port 22. Note that if the desired flow rate is slow enough, the first pump 70 may be used as an alternative to the steps described above in this paragraph. In this case, the controller 12 would leave the additional valve 90 closed, and would issue an appropriate first signal to actuate the first pump 70 instead of the bidirectional pump. The first pump 70 would then draw saline in from the central fluid path 40 and pump it out through the catheter outlet 80. Meanwhile, replacement saline flows into the central fluid path 40 via the second inlet port 22.

Because the bidirectional pump 50 and the first pump 70 are both peristaltic pumps, during the time either one of those pumps are pumping, pressure variations will be induced in the central fluid path 40.

The controller 12 monitors these pressure variations to determine the volume that has been pumped and/or the flow rate. After a particular number of pressure variations has occurred (which corresponds to the volume requested by the operator), the controller turns off whichever pump 50, 70 is active by issuing an appropriate second signal or first signal.

Finally, the controller 12 instructs the touchscreen 15T to return to the state depicted in FIG. 5A (i.e., the home screen), and waits for further instructions to arrive via the touchscreen 15T.

Injecting the Contrast Agent: If the operator wants to inject contrast agent when the home screen is visible, the operator presses the "inject contrast" button on the touchscreen 15T. Based on instructions from the controller 12, the touchscreen 15T will switch to the state depicted in FIG. 5C, which asks the operator to specify the volume and/or flow rate for the contrast injection. Additional screens of the user interface (not shown) are presented to the operator so that the operator can set the volume and/or flow rate to the desired level. After the operator has specified the desired parameters, the operator presses the button 15B to initiate injection of the contrast agent. The controller 12 recognizes that the button 15B has been pressed, and initiates a sequence that is very similar to the saline-injection sequence described above, except that the controller 12 starts the procedure by setting the at least one control input to the third state. This causes the first actuator 35 to move the at least one valve 30 to a position where cam lobe 33 opens the fluid flow path between the central fluid path 40 and the third inlet port 23. The remaining lobes of the cam 31, 32 close the fluid flow paths between the central fluid path and the other inlet ports 21, 22. Subsequently, when the bidirectional pump 50 is actuated in its first mode, the apparatus 10 will pump contrast agent through the system and out the catheter port 80 (instead of saline).

After the contrast agent has been injected, the controller 12 instructs the touchscreen 15T to return to the state depicted in FIG. 5A (i.e., the home screen), and waits for further instructions to arrive via the touchscreen 15T.

Note that before the contrast agent is injected, the balloon 130 at the distal end of the catheter 100 will typically be inflated, and the flow of the contrast agent will be observed using fluoroscopy. If it turns out that the distal tip of the catheter is in the correct position and the balloon provides a good seal, the procedure can continue to the bead injection step. If, on the other hand, the distal tip of the catheter is not in the best position for injecting the beads, the balloon 130 is deflated and the position of the catheter is adjusted. The saline-injection and contrast-injection-with-fluoro steps can then be repeated until the distal tip of the catheter is in the correct spot for injecting the beads.

Injecting the Embolic Beads: Assuming that the home screen depicted in FIG. 5A is visible, once the distal tip of the catheter is in the correct spot for injecting the beads, the operator can initiate injection of the embolic beads by pressing the "inject beads" button on the touchscreen 15T. Based on instructions from the controller 12, the touchscreen 15T will switch to the state depicted in FIG. 5D, which asks the operator to specify the volume of beads that will be injected via the catheter. Additional screens of the user interface (not shown) are presented to the operator so that the operator can set the volume to the desired level. After the operator has specified the desired parameters, the operator presses the button 15B to initiate injection of the beads. The controller 12 recognizes that the button 15B has been pressed, and initiates the following sequence for injecting the beads.

Notably, because (a) the embolic beads must be suspended in a carrier liquid when they are injected and (b) the embolic beads will ordinarily settle within the liquid due to the operation of gravity, the embolic beads and the carrier liquid must be mixed together immediately prior to the injection of the bead/liquid mixture.

Recall that (as described above in the connection phase) a syringe 200 (which contains a mixture of embolic beads and a liquid) was previously connected to the first inlet port 21. The controller 12 orchestrates the mixing of the embolic beads and the liquid by instructing the bidirectional pump 50 to pump the mixture contained in the syringe 200 into the reservoir 60, and subsequently pump the mixture back from the reservoir 60 into the syringe 200. This two-way pumping will temporarily suspend the embolic beads within the liquid. Then, before the embolic beads have a chance to settle (e.g., within 10 seconds, or within one minute if the buoyancies of the embolic beads and the liquid are sufficiently close), the controller 12 instructs the first pump 70 to pump the mixture contained in the syringe 200 into the catheter 100 via the catheter outlet 80.

Additional details of this procedure described in the previous paragraph will now be provided. The first half of the mixing procedure uses the bidirectional pump 50 to pump the mixture contained in the syringe 200 into the reservoir 60. The controller 12 makes this happen by initiates the following sequence after it recognizes that the button 15B has been pressed.

First, the controller 12 sets the at least one control input to the first state. This causes the first actuator 35 to move the at least one valve 30 to a position where cam lobe 31 opens the fluid flow path between the central fluid path 40 and the first inlet port 21. The remaining cam lobes 32, 33 close the fluid flow paths between the central fluid path and the other inlet ports 22, 23.

When the first actuator 35 reports that it has moved to the appropriate position, the controller 12 stops movement of the first actuator 35.

The controller 12 sends a signal to the additional actuator 95 so that the additional actuator 95 closes the additional valve 90 (or, alternatively, to verify that it has been previously moved to the closed state). Then, the controller 12 issues a second signal to actuate the bidirectional pump 50 in its first mode so that it pumps the mixture from its first orifice to its second orifice. Because the additional valve 90 is closed, the mixture exiting the bidirectional pump 50 will flow into the reservoir 60. Meanwhile, replacement mixture flows into the central fluid path 40 via the first inlet port 21.

Because the bidirectional pump 50 is a peristaltic pump, pressure variations will be induced in the central fluid path 40 during the pumping. After the entire contents of the syringe is pumped out, a large rise in pressure will occur. The first pressure sensor 45 will detect this large rise in pressure and report that back to the controller 12. When the controller 12 sees that the large rise in pressure has occurred, the controller 12 realizes that the syringe 200 is now empty. In response to this realization, the controller 12 initiates the second half of the mixing procedure.

Alternatively, instead of waiting for a pressure spike, the controller 12 can monitor the periodic changes in pressure that occur during pumping (e.g., as detected by the first pressure sensor 45, as described above in connection with pumping the saline), and use this information to determine the volume that has been pumped from the syringe 200 into the reservoir 60. When the controller recognizes that a sufficiently large volume has been pumped out of the syringe 200 (e.g., after 9 cc have been pumped out of a syringe 200 that holds 10 cc), the controller initiates the second half of the mixing procedure.

The controller 12 initiates the second half of the mixing procedure (i.e., pumping the mixture back from the reservoir 60 into the syringe 200) by issuing a second control signal to actuate the bidirectional pump 50 in its second mode so that it pumps the mixture from its second orifice to its first orifice. Because the additional valve 90 is closed, the mixture in the reservoir 60 will be pumped back up into the syringe 200.

The controller 12 monitors these pressure variations that are reported by the first pressure sensor 45 with the end goal of pumping a second quantity of liquid from the reservoir 60 back into the syringe 200, wherein the second quantity is smaller than the quantity that was previously pumped from the syringe 200 into the reservoir 60. Ensuring that the amount of fluid that is pumped from the reservoir 60 back up into the syringe 200 is smaller (e.g., at least 10% smaller) than the original amount that was pumped from the syringe 200 into the reservoir 60 advantageously minimizes the risk of introducing air bubbles into the catheter. This is because bubbles will be trapped within the reservoir 60 by operation of gravity and/or surface tension. More specifically, surface tension will tend to cause the bubbles to adhere to the syringe/reservoir walls, and buoyancy/gravity will tend to cause the bubbles to rise to the top of the syringe/reservoir. Thus, when the orifice of the syringe 200 and the orifice of the reservoir 60 are positioned near the bottom of the syringe/reservoir (which is preferably the case), the liquid will be expelled preferentially and the bubbles will remain trapped in the syringe/reservoir (as long as the plunger does not travel far enough to physically force them out).

Notably, both halves of the mixing procedure make use of the bidirectional pump 50. This pump is used because it has a higher flow rate than the first pump 70, and its higher flow rate facilitates mixing of the embolic beads and the liquid that are supplied from the syringe 200. In some embodiments, the flow rate of the bidirectional pump 50 is greater than 30 cc/min. In some embodiments, the bidirectional pump 50 has an output pressure of at least 0.9 atm. The mixing procedure may take up to 60 seconds, depending on the properties of the therapeutic (viscosity, density, requirement to not over-shear).

As noted above, the first inlet port 21 is positioned with respect to the housing so that when the base rests on a horizontal surface and a syringe 200 is mated with the first inlet port 21, the syringe will be oriented vertically with respect to the horizontal surface, plus or minus 300 (or, in some preferred embodiments, plus or minus 15°). This substantially vertical orientation provides a number of benefits during the mixing procedure, including that air bubbles that detach from the inside surface of the syringe will be driven to the plunger, and away from the fluid entering the patient. When the syringe 200 is transparent, the following benefits are also provided. (1) The user can visually confirm that mixing of the embolic beads is occurring, and that the embolic beads remain suspended in the liquid (bead settling due to gravity is a well known issue which can clog the catheter, and deliver unexpectedly high or low doses of embolic beads). (2) The user can visually confirm that the mixing procedure is occurring. And (3) The user can visually confirm that the embolic beads are being pumped out of the syringe, and even visually estimate the volume and rate.

After both halves of the mixing procedure have been executed, the next step is the injection of the embolic beads. In some preferred embodiments, the controller 12 requests confirmation from the user (e.g., via the user interface 15) that the mixing procedure was successful and that the embolic beads are suspended in the liquid within the syringe 200 before injecting the embolic beads.

The injection of the embolic beads via the catheter 100 proceeds as follows. The controller 12 leaves the at least one control input in its first state, which leaves the first actuator 35 at the position where the at least one valve 30 opens the fluid flow path between the central fluid path 40 and the first inlet port 21. The controller 12 also leaves the additional actuator 95 alone, so that the additional valve 90 stays closed.

Next, the controller 12 controls the first signal, which actuates the first pump 50. This causes the first pump 70 to pump the embolic beads and the liquid from the central fluid path 40 out to the catheter 100 via the catheter outlet 80. Meanwhile, replacement beads and liquid flow into the central fluid path 40 from the syringe 200 via the first inlet port 21.

In some preferred embodiments, the controller 12 controls the pumping rate of the first pump 70 so that the mixture of embolic beads and liquid exiting the distal end of the catheter 100 maintains a laminar flow. Maintaining laminar flow is advantageous because it dramatically reduces the risk that embolic beads will reflux and subsequently traveled to non-target portions of the subject's anatomy. One approach for maintaining laminar flow relies on pressure readings obtained by the distal pressure sensor 140.

Flows with Reynold's Number below ~2,300 are generally considered to be in the laminar regime. Materials passed through the catheter and into the blood stream generally have densities between 1 g/cc and 1.5 g/cc, and viscosities between 0.80 cP and 24 cP. In one example, we assume that the catheter 100 has a flow lumen of 0.5 mm, and that the blood vessels have an inner diameter between 1 and 6 mm. Based on these factors and known pressure differential (i.e., between the pressure measured by the distal pressure sensor 140 and the pressure measured by the first pressure sensor 45), we can use Hagen Poiseuille Flow and Poiseuille's Law equations to determine the correct volumetric flow rate to deliver laminar flow. As the local pressure (i.e., local at the target anatomy) changes, so too can flow rate change to maintain laminar flow.

$$Re = \frac{\rho u L}{\mu} \quad \text{Equation (1): Reynold's Number}$$

$$\Delta P = \frac{8\mu L Q}{\pi R^4} \quad \text{Equation (2): Hagen Poiseuille Flow}$$

$$Q = -\frac{\Delta P \pi R^4}{8\mu \Delta x} \quad \text{Equation (3): Poiseuille's Law}$$

Where P=Pressure between two ends of a pipe; L=length; R=radius of pipe; Q=Volumetric flow rate; µ=dynamic viscosity; ρ=Density; and u=velocity.

If we assume worst case parameters of ρ=1.5 g/cc, u=0.8 m/s; L=1.5 m; and µ=0.0008 Ns/m², equation (1) gives us a Reynolds number of 2250. And if we assume best case parameters of ρ=1 g/cc; u=0.7 m/s; L=1.1 m; and µ=0.0024 Ns/m², equation (1) gives us a Reynolds number of 320.8. Plugging the worst-case values into equations (2) and (3) yields a worst-case ΔP of 148633 Pa (i.e., 21.56 PSI). And plugging the best-case values into equations (2) and (3) yields a best-case ΔP of 9561.2 (i.e., 1.387 PSI).

Figure 6:
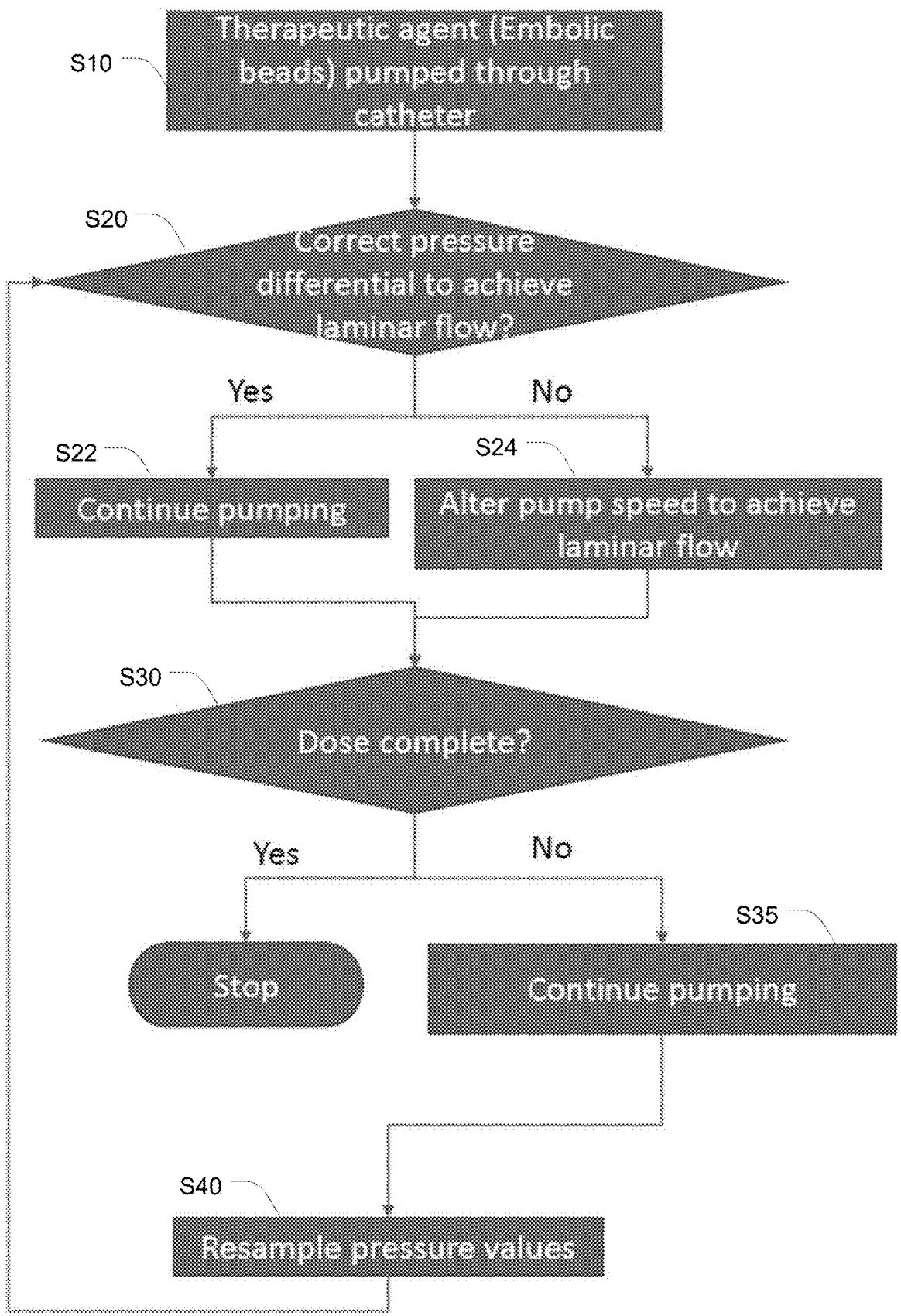
FIG. 6 depicts an example of a control loop that can be executed by the controller to maintain laminar flow.

FIG. 6 depicts an example of a control loop that can be executed by the controller 12 to maintain laminar flow. In step S10, the embolic beads are pumped through the catheter 100. In step S20, the controller 12 computes the pressure differential between the pressure measured by the first pressure sensor 45 and the distal pressure sensor 140. Using the equations above, the controller determines whether the measured pressure differential is expected to achieve laminar flow. If the answer is yes, then pumping continues in step S22. If the answer is no, the controller 12 alters the pump speed to achieve laminar flow in step S24. Next, in step S30, the controller 12 determines whether the dose is complete (i.e., whether a sufficient volume of the liquid/bead mixture has been pumped through the catheter 100). If the answer is yes, the procedure stops. If the answer is no, the controller 12 continues pumping in step S35. Then, in step S40, the controller 12 obtains new samples of pressure readings from the first pressure sensor 45 and the distal pressure sensor 140, after which processing returns to step S20.

Figure 7:
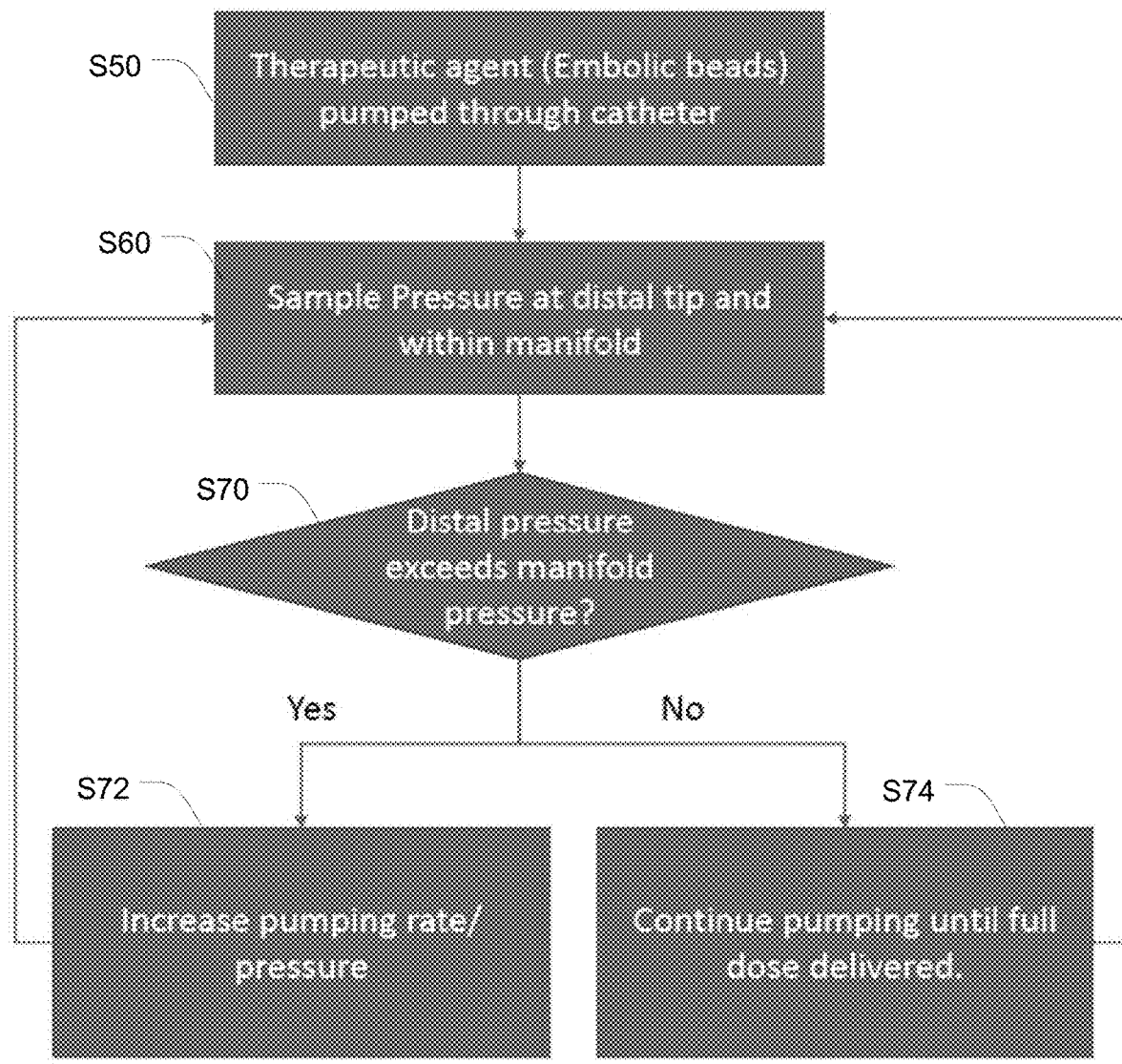
FIG. 7 depicts an example of a pressure feedback loop that can be executed by the controller to adjust the pumping pressure.

FIG. 7 depicts an example of a pressure feedback loop that can be executed by the controller 12 to adjust the pumping pressure. In step S50, the liquid/bead mixture is being pumped through the catheter 100. In step S60, the controller 12 obtains readings from the first pressure sensor 45 and the distal pressure sensor 140. Next, in step S70, the controller 12 determines whether the reading from the distal pressure sensor 140 exceeds the reading from the first pressure sensor 45. If the answer is yes, the controller 12 increases the pumping rate/pressure of the first pump 70 in step S72 (e.g., by increasing the voltage that is applied to the first pump 70); and processing returns to step S60. If the answer is no, the controller 12 does not change the rate/pressure in step S74, in which case the first pump 70 will continue pumping at the same rate/pressure; and processing returns to step S60.

Because the first pump 70 is a peristaltic pump, pressure variations will be induced in the central fluid path 40 during the pumping.

The controller 12 monitors these pressure variations to determine the volume that has been pumped and/or the flow rate. After a particular number of pressure variations has occurred (which corresponds to the volume requested by the operator), the controller turns off the first pump 50.

Finally, the controller 12 instructs the touchscreen 15T to return to the state depicted in FIG. 5A (i.e., the home screen), and waits for further instructions to arrive via the touchscreen 15T. At this point, the operator has the option to continue the procedure by pressing one of the buttons to inject saline, contrast, or an additional quantity of embolic beads. Alternatively, the operator can end the procedure by pressing the "end procedure" button.

Notably, in order to maintain laminar flow and to inject a precise quantity of embolic beads into a patient, the first pump 70 must operate with a relatively high degree of precision. Indeed, the first pump 70 described above can inject the embolic beads at a slower rate than is possible by hand. Designing a single pump system in which a single pump both mixes the embolic beads with the liquid and also injects the mixture with the required degree of precision would be difficult and expensive. The dual-pump system described herein, which uses two different pumps 50, 70 to respectively perform mixing and injection, avoids this problem. This is because one pump (i.e., the bidirectional pump 50) is optimized for high-speed operation, while the other pump (i.e., the first pump 70) is optimized for low speed operation with high precision. In some embodiments, the flow rate of the bidirectional pump 50 is greater than 30 cc/min, and the flow rate of the first pump 70 is less than 10 cc/min. And in some embodiments, the flow rate of the bidirectional pump is at least five times greater than the flow rate of the first pump.

Finally, while the embodiments described above are explained in the context of delivering embolic beads into an artery by first mixing the embolic beads with a liquid, and subsequently injecting the mixture, the same embodiments may be used to deliver other therapeutic substances (e.g., liquids and/or particles other than embolic beads) into an artery by first mixing the therapeutic substance with a liquid, and subsequently injecting the mixture.

While the present invention has been disclosed with reference to certain embodiments, numerous modifications, alterations, and changes to the described embodiments are possible without departing from the sphere and scope of the present invention, as defined in the appended claims. Accordingly, it is intended that the present invention not be limited to the described embodiments, but that it has the full scope defined by the language of the following claims, and equivalents thereof.

What is claimed is:

1. An apparatus for controlling delivery of a suspension of a therapeutic substance dispersed within a liquid, the apparatus comprising:
a first inlet port;
a second inlet port;
a third inlet port;
at least one valve arranged to selectively open or close a first fluid-flow path between the first inlet port and a central fluid path, to selectively open or close a second fluid-flow path between the second inlet port and the central fluid path, and to selectively open or close a third fluid-flow path between the third inlet port and the central fluid path;
an outlet port;
a first pump having an inlet in fluid communication with the central fluid path and an outlet in fluid communication with the outlet port, wherein the first pump is configured to, when actuated, pump liquid from the central fluid path to the outlet port at a first flow rate;
a fluid-tight reservoir;
a bidirectional pump having a first orifice in fluid communication with the central fluid path and a second orifice in fluid communication with the reservoir, wherein the bidirectional pump is configured to, when actuated in a first mode, pump liquid from the first orifice to the second orifice at a flow rate that is at least double the first flow rate, and wherein the bidirectional pump is configured to, when actuated in a second mode, pump liquid from the second orifice to the first orifice;
a first actuator configured to, in response to a state of at least one control input, control the at least one valve;
an additional valve arranged to selectively open or close a fluid-flow path between the second orifice of the bidirectional pump and the outlet of the first pump;
an additional actuator configured to, in response to a state of an additional control input, selectively open or close the additional valve; and
a controller configured to (i) control the state of the at least one control input, (ii) control the state of a first signal that actuates the first pump, (iii) control the state of at least one second signal that actuates the bidirectional pump in either the first mode or the second mode, and (iv) control the state of the additional control input,
wherein the first pump comprises a peristaltic pump and wherein the bidirectional pump comprises a peristaltic pump,
wherein the first fluid-flow path comprises tubing that runs between the first inlet port and the central fluid path, and wherein the at least one valve comprises a first pinch valve arranged to selectively open or close the first fluid-flow path,
wherein the second fluid-flow path comprises tubing that runs between the second inlet port and the central fluid path, and wherein the at least one valve further comprises a second pinch valve arranged to selectively open or close the second fluid-flow path,
wherein the third fluid-flow path comprises tubing that runs between the third inlet port and the central fluid path, and wherein the at least one valve comprises a third pinch valve arranged to selectively open or close the third fluid-flow path, and
wherein the first actuator comprises a first cam positioned to selectively open or close the first pinch valve, a second cam positioned to selectively open or close the second pinch valve, and a third cam positioned to selectively open or close the third pinch valve.

2. The apparatus of claim 1, further comprising:
a first pressure sensor positioned to measure pressure in the central fluid path, wherein the first pressure sensor outputs data indicative of a measured pressure; and
a conductivity sensor positioned to measure conductivity in a fluid-flow line that leads to the outlet port, wherein the conductivity sensor outputs data indicative of a measured conductivity,
wherein the controller is further configured to accept the data output by the first pressure sensor and to accept the data output by the conductivity sensor.

3. The apparatus of claim 2,
wherein the first inlet port comprises a female Luer inlet,
wherein the second inlet port comprises a female Luer inlet,
wherein the third inlet port comprises a female Luer inlet, and
wherein the outlet port comprises a male Luer outlet.

4. The apparatus of claim 1, wherein when actuated in the first mode, the bidirectional pump pumps liquid from the first orifice to the second orifice at the flow rate that is at least five times the first flow rate.

5. The apparatus of claim 1, wherein when actuated in the first mode, the bidirectional pump pumps the liquid from the first orifice to the second orifice at the flow rate greater than 30 cc/min, and wherein the first flow rate is less than 10 cc/min.

6. The apparatus of claim 1, further comprising a first pressure sensor positioned to measure pressure in the central fluid path, wherein the first pressure sensor outputs data indicative of a measured pressure, and wherein the controller is further configured to accept the data output by the first pressure sensor.

7. An apparatus for controlling delivery of a suspension of a therapeutic substance dispersed within a liquid, the apparatus comprising:
a first inlet port;
a second inlet port;
at least one valve arranged to selectively open or close a first fluid-flow path between the first inlet port and a central fluid path and to selectively open or close a second fluid-flow path between the second inlet port and the central fluid path;
an outlet port;
a first pump having an inlet in fluid communication with the central fluid path and an outlet in fluid communication with the outlet port, wherein the first pump is configured to, when actuated, pump liquid from the central fluid path to the outlet port at a first flow rate;
a fluid-tight reservoir;
a bidirectional pump having a first orifice in fluid communication with the central fluid path and a second orifice in fluid communication with the reservoir, wherein the bidirectional pump is configured to, when actuated in a first mode, pump liquid from the first orifice to the second orifice at a flow rate that is at least double the first flow rate, and wherein the bidirectional pump is configured to, when actuated in a second mode, pump liquid from the second orifice to the first orifice;
a first actuator configured to, in response to a state of at least one control input, control the at least one valve;
a first pressure sensor positioned to measure pressure in the central fluid path, wherein the first pressure sensor outputs data indicative of a measured pressure; and
a controller configured to (i) control the state of the at least one control input, (ii) control the state of a first signal that actuates the first pump, and (iii) control the state of at least one second signal that actuates the bidirectional pump in either the first mode or the second mode,
wherein the controller is further configured to accept the data output by the first pressure sensor, and to determine a flow rate and/or a flow volume by tracking at least one of transitions, peaks, and troughs in the data output by the first pressure sensor.

8. The apparatus of claim 7, wherein the controller is further configured to control the state of the at least one second signal that actuates the bidirectional pump based on the data output by the first pressure sensor so that (a) the bidirectional pump pumps a first quantity of liquid from the first inlet port to the reservoir until a large rise in pressure occurs, and (b) the bidirectional pump subsequently pumps a second quantity of liquid from the reservoir to the first inlet port, wherein the second quantity is smaller than the first quantity.

9. The apparatus of claim 7, further comprising a catheter configured to mate with the outlet port, wherein the catheter includes a second pressure sensor positioned at a distal end of the catheter, wherein the second pressure sensor outputs data indicative of a measured pressure, and wherein the controller is further configured to accept the data output by the second pressure sensor.

10. The apparatus of claim 9, wherein the controller is further configured to control the state of the first signal so as to adjust a pumping rate of the first pump based on the data output by the first pressure sensor and the data output by the second pressure sensor.

11. The apparatus of claim 9, wherein the controller is further configured to control the state of the first signal so as to increase a pumping rate of the first pump if a pressure measured by the second pressure sensor exceeds a pressure measured by the first pressure sensor.

12. The apparatus of claim 7, wherein the first inlet port, the second inlet port, the at least one valve, the outlet port, the first pump, and the bidirectional pump are housed by a housing, the housing having a base,
wherein the first inlet port is positioned with respect to the housing so that when the base rests on a horizontal surface and a syringe is mated with the first inlet port, the syringe will be oriented vertically with respect to the horizontal surface, plus or minus 30°.

13. The apparatus of claim 7, wherein the first inlet port, the second inlet port, the at least one valve, the outlet port, the first pump, and the bidirectional pump are housed by a housing, the housing having a base,
wherein the first inlet port is positioned with respect to the housing so that when the base rests on a horizontal surface and a syringe is mated with the first inlet port, the syringe will be oriented vertically with respect to the horizontal surface, plus or minus 15°.

14. The apparatus of claim 7, wherein the controller is further configured to control the state of the first signal that actuates the first pump so that when the first pump is used to pump a liquid through a catheter that has been connected to the outlet port, the liquid exiting the catheter has a laminar flow.

15. An apparatus for controlling delivery of a suspension of a therapeutic substance dispersed within a liquid, the apparatus comprising:
a first inlet port;
a second inlet port;
at least one valve arranged to selectively open or close a first fluid-flow path between the first inlet port and a central fluid path and to selectively open or close a second fluid-flow path between the second inlet port and the central fluid path;

an outlet port;

a first pump having an inlet in fluid communication with the central fluid path and an outlet in fluid communication with the outlet port, wherein the first pump is configured to, when actuated, pump liquid from the central fluid path to the outlet port at a first flow rate;

a fluid-tight reservoir;

a bidirectional pump having a first orifice in fluid communication with the central fluid path and a second orifice in fluid communication with the reservoir, wherein the bidirectional pump is configured to, when actuated in a first mode, pump liquid from the first orifice to the second orifice at a flow rate that is at least double the first flow rate, and wherein the bidirectional pump is configured to, when actuated in a second mode, pump liquid from the second orifice to the first orifice; and a first actuator configured to, in response to a state of at least one control input, control the at least one valve;

a first pressure sensor positioned to measure pressure in the central fluid path, wherein the first pressure sensor outputs data indicative of a measured pressure;

a user interface configured to generate an output signal in response to user input; and a controller configured to (i) control the state of the at least one control input, (ii) control the state of a first signal that actuates the first pump, and (iii) control the state of at least one second signal that actuates the bidirectional pump in either the first mode or the second mode, wherein the controller is further configured to accept the data output by the first pressure sensor, and wherein the controller is further configured to, in response to the output signal generated by the user interface,
 (a) control the state of the at least one control input so that the first actuator controls the at least one valve so that the at least one valve opens the first fluid-flow path and closes the second fluid-flow path,
 (b) subsequently control the state of the at least one second signal that actuates the bidirectional pump based on the data output by the first pressure sensor so that the bidirectional pump pumps a first quantity of liquid from the first inlet port to the reservoir until the data indicative of the measured pressure reveals a large rise in pressure,
 (c) subsequently control the state of the at least one second signal that actuates the bidirectional pump so that the bidirectional pump pumps a second quantity of liquid from the reservoir to the first inlet port, wherein the second quantity is smaller than the first quantity, and
 (d) subsequently control the state of the first signal that actuates the first pump so that the first pump pumps liquid from the first inlet port to the outlet port.

* * * * *